United States Patent [19]

Ellinwood, Jr. et al.

[11] Patent Number: 5,739,136
[45] Date of Patent: Apr. 14, 1998

[54] INTRAORAL DOSING METHOD OF ADMINISTERING MEDICAMENTS

[76] Inventors: Everett H. Ellinwood, Jr., 3519 Tonbridge Way, Durham, N.C. 27707; Samir K. Gupta, 807 Woodbridge Common Way, Iselin, N.J. 08830

[21] Appl. No.: 622,829

[22] Filed: Mar. 27, 1996

Related U.S. Application Data

[63] Continuation-in-part of Ser. No. 321,246, Oct. 11, 1994, Pat. No. 5,504,086, which is a continuation-in-part of Ser. No. 38,911, Mar. 29, 1993, Pat. No. 5,354,780, which is a continuation-in-part of Ser. No. 703,049, May 17, 1991, Pat. No. 5,198,436, which is a continuation of Ser. No. 422,992, Oct. 17, 1989, abandoned.

[51] Int. Cl.$^6$ .................................................. A61K 31/495
[52] U.S. Cl. .................................................... 514/252
[58] Field of Search ......................................... 514/252

[56] References Cited

PUBLICATIONS

Posner et al., *European Journal of Clinical Pharmacology*, "The Disposition of Bupropion and Its Metabolites in Healthy Male Volunteers After Single and Multiple Doses", vol. 29, pp. 97–103 (1985).

Workman et al., *American Journal of Psychiatry*, "Trazodone Induction of Migraine Headache Through mCPP", vol. 149, p. 5 (May, 1992).

DeVane et al., *Fundamentals of Monitoring Psychoactive Drug Therapy*, pp. 44–46 (1990).

Golden et al., *Archives of General Psychiatry*, "Bupropion in Depression", vol. 45, pp. 145–149 (Feb., 1988).

*Primary Examiner*—Zohreh Fay
*Attorney, Agent, or Firm*—Richard E. Jenkins, P.A.

[57] ABSTRACT

A method of therapeutically administering certain medicaments in order to maximize the desired effects and minimize the unwanted metabolite effects on the human body, including the central nervous system, in order to maximize therapeutic effects, such as anti-anxiety, anticonvulsant and hypnotic effects, and minimize unwanted side effects, such as ataxic and incoordination effects, of the drug. Also, a method of sublingual or buccal administration of certain medicaments in order to decrease metabolism of the medicaments to unwanted metabolites.

4 Claims, 10 Drawing Sheets

Figure 1. Sublingual VS Oral Q and DOQ, Single Dosing

Figure 2. Sublingual VS Oral Q and DOQ, Single Dosing

Figure 3. Sublingual VS Oral Q and DOQ, Multiple Dosing

INTRAORAL DOSING METHOD OF ADMINISTERING MEDICAMENTS

RELATED APPLICATIONS

This application is a continuation-in-part of application Ser. No. 08/321,246 filed on Oct. 11, 1994, U.S. Pat. No. 5,504,086 which is a continuation-in-part of application Ser. No. 08/038,911 filed on Mar. 29, 1993 and issued on Oct. 11, 1994 as U.S. Pat. No. 5,354,780, which is a continuation-in-part of application of Ser. No. 07/703,049 filed on May 17, 1991 and issued on Mar. 30, 1993 as U.S. Pat. No. 5,198,436, which is a continuation application of Ser. No. 07/422,992 filed on Oct. 17, 1989 and now abandoned.

TECHNICAL FIELD

This invention relates to a novel method of administering certain medicaments which surprisingly results in a maximization of the effect on the human body, including the central nervous system receptors, due to the desired medicament and minimization of the effect on the human body, including the central nervous system receptors, due to the unwanted metabolite from the medicament so as to maximize therapeutic effects, such as antianxiety, anticonvulsant, and/or hypnotic effects, and to minimize unwanted side effects, such as ataxic and incoordination effects, of the medicament thereon.

More particularly, when certain medicaments that generate metabolites which are unwanted (the adversive metabolites are increased by gastrointestinal tract absorption and subsequent portal vein entry to the liver, for instance when the medicament is orally swallowed), then, in accordance with the present invention, the intraoral, i.e. buccal or sublingual administration, of such medicaments significantly reduces change of the medicaments into unwanted metabolites.

BACKGROUND ART

The most pertinent prior art reference known to applicants is U.S. Pat. No. 4,229,447 to Porter which discloses a method of administering certain benzodiazepines sublingually and buccally. Porter specifically mentions the sublingual or buccal administration of diazepam, lorazepam, oxazepam, temazepam and chlorodiazepoxide and describes two generic structures of benzodiazepines that may be administered sublingually or buccally.

The compound shown below is contemplated by the generic structures in Porter. All of the benzodiazepines disclosed and the generic structure described in Porter are $BZ_1$-$BZ_2$ receptor non-specific since they lack the trifluoro ethyl group in the N position of the "B" ring which confers $BZ_1$ specificity.

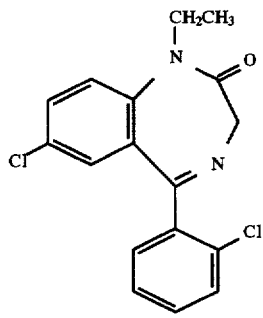

Porter's method is based on the rapid buccal or sublingual absorption of selected benzodiazepines to attain effective plasma concentration more rapidly than oral administration. In contrast, while parenteral administration provides a rapid rise of blood levels of the benzodiazepines, parenteral administration is frequently accompanied by pain and irritation at the injection site and may require sterilization of the preparatives and the hypodermic syringes.

Porter points out that the intraoral, i.e. buccal or sublingual administration, of lipid soluble benzodiazepines results in therapeutic levels resembling parenteral administration without some of the problems associated therewith. Porter's administration technique for benzodiazepines in general builds on a long established knowledge in pharmacology that drugs absorbed in the intraoral route give rise to more rapid absorption than when swallowed into the stomach. What is not recognized by Porter, however, are concerns with first-pass metabolism which can be avoided either with the sublingual or parenteral route of drug administration of certain benzodiazepines.

Porter does not recognize that first-pass metabolism designates the drug intestinal absorption with subsequent entry directly into the portal blood supply leading to the liver and that the liver in turn rapidly absorbs and metabolizes the drug with its first-pass high concentration through the liver. In addition, some first pass metabolism may occur during the absorption process into the intestine. Thus, large amounts of the drug may never be seen by the systemic circulation or drug effect site. Porter further does not recognize that the more rapid metabolism via the first-pass metabolism route can lead to accelerated desalkylation with formation of high plasma concentrations of an unwanted metabolite.

Thus, applicants' concern with avoiding the degradation of the parent compound and its desired positive effect and the metabolism of the parent compound to an undesired metabolite is neither recognized nor addressed by Porter, which only addresses the ability of the oral mucous membranes to absorb certain benzodiazepines fast and achieve high plasma levels thereof quickly.

The specific drug for which this phenomenon was demonstrated by Porter was lorazepam which has a simple metabolism that results in it not being metabolized to active compounds. Also, and very significantly, the issue of human nervous system receptor specificity and activation for $BZ_1$ and $BZ_2$ type receptors is not recognized by Porter either generally or with reference specifically to trifluorobenzodiazepines.

U.S. Pat. No. 3,694,552 to Hester discloses that 3-(5-phenyl-3H-1,4-benzodiazepine-2-yl) carbazic acid alkyl esters, which are useful as sedatives, hypnotics, tranquilizers, muscle relaxants and anticonvulsants, can be administered sublingually. Subsequently issued U.S. Pat.

No. 4,444,781 to Hester specifically teaches that 8-chloro-1-methanol-6-(o-chlorophenyl)-4H-s-triazolo[4,3-a][1,4]-benzodiazepine therapeutic compounds, which are useful as soporifics, can be suitably prepared for sublingual use.

Also, U.S. Pat. No. 4,009,271 to vonBebenburg et al. discloses that 6-aza-3H-1,4-benzodiazepines and 6-aza-1,2-dihydro-3H-1,4-benzodiazepines (which have pharmacodynamic properties including psychosedative and anxiolytic properties as well as antiphlogistic properties) can be administered enterally, parenterally, orally or perlingually.

The chemical formula of nefazodone is 2-(3-(4-(3-chlorophenyl)-1-piperazinyl)propyl-5-ethyl-2,4-dihydro-4-(2-phenoxyethyl)-3H-1,2,4-triazol-3-one hydrochloride.

Patients with obsessive compulsive disorder respond to meta-chlorophenylpiperazine (hereinafter, abbreviated as mCPP), an undesirable metabolite of nefazodone, by becoming much more anxious and obsessional, as reported by Zohar et al. in "Serotonergic Responsivity in Obsessive Compulsive Disorder: Comparison of Patients and Healthy Controls", Arch. Gen. Psychiatry, Vol. 44, pp. 946–951 (1987). The peak in the anxiousness and obsessional behaviors is observed within 3 hours of mCPP administration and the duration of the worsening ranges from several hours to as much as 48 hours. Much more significantly, mCPP induced a high rate of emergence of entirely new obsessions or the reoccurrence of obsessions that had not been present in the patients for several months. Patients also reported being more depressed and dysphoric.

More specifically, Zohar et al. administered 0.5 mg/kg of mCPP orally to subjects in eliciting their obsessional symptoms. The peak plasma concentration in the control patients was 33.4±17.34 ng/ml, whereas, in the obsessional patients, the peak plasma concentration inducing the obsessional behavior was 26.9 ng/ml±12.33.

Furthermore, Hollander et al., in "Serotonergic Noradrenergic Sensitivity in Obsessive Compulsive Disorder: Behavioral Findings", Am. J. Psychiatry, Vol. 1945, pp. 1015–1017 (1988), have reported many of these obsessional worsening effects in obsessive compulsive patients.

Additionally, Kahn et al., in "Behavioral indications for Serotonin Receptor Hypersensitivity in Panic Disorder", Psychiatry Res., Vol. 25, pp. 101–104 (1988), have reported mCPP induces anxiety in a group of panic disorder patients.

Moreover, Walsh et al., as reported in "Neuroendocrine and Temperature Effects of Nefazodone in Healthy Volunteers", Biol. Psychiatry, Vol. 33, pp. 115–119 (1933), administered oral doses of 50 mg and 100 mg of nefazodone to normal subjects and measured nefazodone and its metabolite mCPP. For the 50 mg does, the nefazodone/mCPP area under the curve (hereinafter, abbreviated as AUC) ratio was 1.58. For the 100 mg dose, the AUC ratio was 1.63, indicting that within the first 3 hours, nefazodone is substantially metabolized to MCPP at levels considerably above the mCPP levels that Zohar et al., supra, found to induce anxiety and obsessional states in susceptible individuals.

In studies in dogs, intravenous dosing of nefazodone reduced plasma mCPP Cmax by 50% from that found with oral dosing, as reported by Shukla et al., in "Pharmacokinetics, Absolute Bioavailability, and Disposition of [$^{14}$C] Nefazodone in the Dog", Drug Metab. Disposition, Vol. 21, No. 3, pp. 502–507 (1993).

Also, a discussion of bupropion and its three major metabolites, erythrohydrobupropion, hydroxybupropion, and threohydrobupropion, as well as the strong relationship of higher hydroxybupropion metabolite concentrations in therapeutically non-responding patients in contrast to responders, can be seen in Posner et al., "The Disposition of Bupropion and Its Metabolites in Healthy Male Volunteers after Single and Multiple Doses", Vol. 29, Eur. J. Clin. Pharmacol., pp. 97–103 (1985) and Bolden et al., "Bupropion in Depression", Vol. 45, Arch. Gen. Psychiatry, pp. 145–149 (February 1988). Hydroxybupropion, therefore, represents an unwanted metabolite.

STATEMENT OF THE INVENTION

It is well known by those practiced in the art that special distribution of enzymatic activity within the gastrointestinal tract and the liver leads to a metabolic zonation for metabolism of drugs. This zonation is noted in peripheral midzonal and pericentral regions of the liver.

Thus, the relative distribution of two or more enzymes with respect to substrate entry point and the relative magnitudes of the enzymatic parameters will have a large impact on the metabolic pathway emphasized. When a drug is swallowed, each of the stomach and the small intestine absorbs it, presenting an opportunity for partial metabolism with subsequent flow to the portal vein entry to the liver. Therefore, differential metabolic zonation is possible if the drug is absorbed by the gastrointestinal tract and distributed to the liver by the portal vein, rather than by the hepatic artery from the general circulation.

Even though this general background information is known to those persons practiced in the art, the specific findings that formation of unwanted metabolites is reduced by sublingual/buccal administration was not known until applicants' unexpected discovery herein.

Accordingly, in accordance with the present invention, provided is an improvement in a method for administering medicament to the human body, including the central nervous system, wherein a therapeutically effective amount of said medicament is intraorally administered (i.e., sublingually or buccally administered) to a human. The improvement comprises selecting a medicament that is metabolized into an unwanted or adversive metabolite which is increased by gastrointestinal tract absorption and subsequent portal vein entry to the liver; and placing the medicament in a suitable intraoral (i.e., sublingual or buccal) formulation. Then, a therapeutically effective amount of the intraoral formulation is intraorally administered so as to bypass the gastrointestinal tract absorption and subsequent portal vein entry to the liver and thereby to decrease formation of the unwanted metabolite. Next, the ratio is increased of medicament to the unwanted metabolite made available to the human body, including the central nervous system, and this intraoral method is utilized over a period of one or more doses to achieve sustained high levels of the medicament relative to the unwanted metabolite.

Also, the specific findings that trifluorobenzodiazepine N-desalkylation is reduced by sublingual/buccal administration was not known until applicants' unexpected discovery with quazepam and halazepam.

Therefore, also in accordance with the present invention, applicants provide a novel method for maximizing the effect of selected trifluorobenzodiazepines including 7-chloro-1-(2,2,2-trifluoroethyl)-5-(o-fluoro phenyl)-1,3-dihydro-2H-1,4-benzodiazepine-2-thione (i.e., quazepam) and 7-chloro-1,3-dihydro-5-phenyl-1-1(2,2,2-trifluoroethyl)-2H-1,4-benzodiazepine-2-one (i.e., halazepam) on benzodiazepine Type I ($BZ_1$) receptors and minimizing the unwanted potent effect of certain metabolites on benzodiazepine Type II ($BZ_2$) receptors of the human central nervous system so as to maximize the antianxiety and anticonvulsant and/or hypnotic effects and to minimize the ataxic and incoordination effects thereon. The method comprises selecting a suitable lipid soluble and $BZ_1$ specific trifluorobenzodiazepine, placing the trifluorobenzodiazepine in a suitable intraoral formulation, and then intraorally administering a therapeutically effective amount of said intraoral formulation so as to bypass the first pass metabolism of said selected trifluorobenzodiazepine in the liver.

The selected trifluorobenzodiazepines with $BZ_1$ specificity are represented by the following structural formula and include:

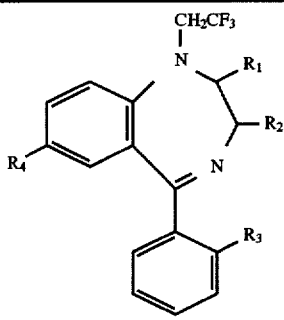

| COMPOUND | $R_1$ | $R_2$ | $R_3$ | $R_4$ |
|---|---|---|---|---|
| 1. HALAZEPAM | =O | H,H | H | Cl |
| 2. 3-OH-HALAZEPAM | =O | OH,H | H | Cl |
| 3. QUAZEPAM (Q) | =S | H,H | F | Cl |
| 4. 2-OXO−Q | =O | H,H | F | Cl |
| 5. 2-OXO-3-OH−Q | =O | OH,H | F | Cl |
| 6. SCH 15698 | H,H | H,H | F | Cl |
| 7. SCH 16893 | H,H | H,H | Cl | Cl |
| 8. SCH 18449 | H,H | H,H | F | Br |
| 9. 3-OH−Q | =S | OH,H | F | Cl |

1. 7-chloro-1-(2,2,2-trifluoroethyl)-5-phenyl-1,3-dihydro-2H-1,4-benzodiazepin-2-one.
2. 7-chloro-1-(2,2,2-trifluoroethyl)-5-phenyl-1,3-dihydro-3-hydroxy-2H-1,3-benzodiazepin-2-one.
3. 7-chloro-1-(2,2,2-trifluoroethyl)-5-(2-fluorophenyl)-1,3-dihydro-2H-1,4-benzodiazepin-2-thione.
4. 7-chloro-1-(2,2,2-trifluoroethyl)-5-(2-fluorophenyl)-1,3-dihydro-2H-1,4-benzodiazepin-2-one.
5. 7-chloro-1-(2,2,2-trifluoroethyl)-5-(2-fluorophenyl)-1,3-dihydro-3-hydroxy-2H-1,4-benzodiazepin-2-one.
6. 7-chloro-1-(2,2,2-trifluoroethyl)-5-(2-fluorophenyl)-1,3-dihydro-2H-1,4-benzodiazepin.
7. 7-chloro-1-(2,2,2-trifluoroethyl)-5-(2-chlorophenyl)-1,3-dihydro-2H-1,4-benzodiazepin.
8. 7-bromo-1-(2,2,2-trifluoroethyl)-5-(2-fluorophenyl)-1,3-dihydro-2H-1,4-benzodiazepin.
9. 7-chloro-1-(2,2,2-trifluoroethyl)-5-(2-fluorophenyl)-1,3-dihydro-3-hydroxy-2H-1,4-benzodiazepin-2-thione.

The trifluorobenzodiazepines referenced above are also lipid soluble. All of the benzodiazepines reported to have $BZ_1$ specificity have a $CH_2CF_3$ group on the nitrogen in the "B" ring. Metabolic loss of this $CH_2CF_3$ group results in a benzodiazepine that is non-specific for the $BZ_1$-$BZ_2$ receptors. Applicants' invention was made possible by the unexpected and surprising discovery from pharmacokinetic studies that sublingual dosing minimizes the desalkylation metabolic pathway leading to the formation of nonspecific metabolites of the selected trifluorobenzodiazepine.

An object of the present invention is to increase the effectiveness of certain selected trifluorobenzodiazepines on human subjects to reduce anxiety and convulsions.

Another object of the present invention is to provide a new administration method which increases the availability of certain selected trifluorobenzodiazepines to the human central nervous system and decreases the amount of undesirable metabolites available thereto.

Still another object of the present invention is to maximize the effect of certain selected trifluorobenzodiazepines on $BZ_1$ receptors of the human central nervous system and minimize their effect on $BZ_2$ receptors.

DETAILED DESCRIPTION OF THE INVENTION

When certain medicaments that generate metabolites which are toxic and thus unwanted (the adversive metabolites are increased by gastro intestinal tract absorption and subsequent portal vein entry to the liver, for instance when the medicament is orally swallowed), then, in accordance with the present invention, the intraoral, i.e. buccal or sublingual administration, of such medicaments significantly reduces change of the medicaments into unwanted or toxic metabolites.

Suitable medicaments useful in accordance with the present invention are those that have the properties of:

(1) an unwanted metabolite, and
(2) the ratio of the unwanted metabolite to the therapeutic drug is substantially reduced by sublingual or buccal administration, in contrast administration by swallowing. Examples of such suitable medicaments include, but are not limited to, a medicament selected from the group consisting of propoxyphene, trifluorobenzodiazepine, nefazodone, trazodone, chlorimipramine, bupropion, and combinations thereof.

More specifically, quazepam, a trifluorobenzodiazepine, is selective for benzodiazepine Type I ($BZ_1$) receptors of the central human nervous system. Action at the $BZ_1$ receptors has been linked to antianxiety and anticonvulsant and/or hypnotic effects, whereas action at $BZ_2$ receptors of the human central nervous system has been linked to muscle relaxation and ataxic effects. N-desalkyl-2-oxoquazepam (DOQ), an active metabolite of quazepam (Q), is $BZ_1$, $BZ_2$ receptor non-specific, and also has a much higher affinity or potency for both receptor types when compared to the $BZ_1$ specific affinity of quazepam (Q). Thus, the higher affinity metabolite (DOQ) of quazepam (Q) contributes substantially to the adverse ataxic and incoordination effects of quazepam on the human central nervous system. In addition, because DOQ has a much longer elimination half-life than the parent quazepam compound (Q), repeated dosing leads to the gradual accumulation of the non-specific, unwanted metabolite, and a greater ratio of DOQ/Q attains over a period of days. Thus, after two to three hours subsequent to an acute dose of quazepam, the DOQ metabolite, both because of its increased gradual accumulation and its greater potency than the parent compound Q, can obviate the advantages of quazepam itself.

Figure 1:
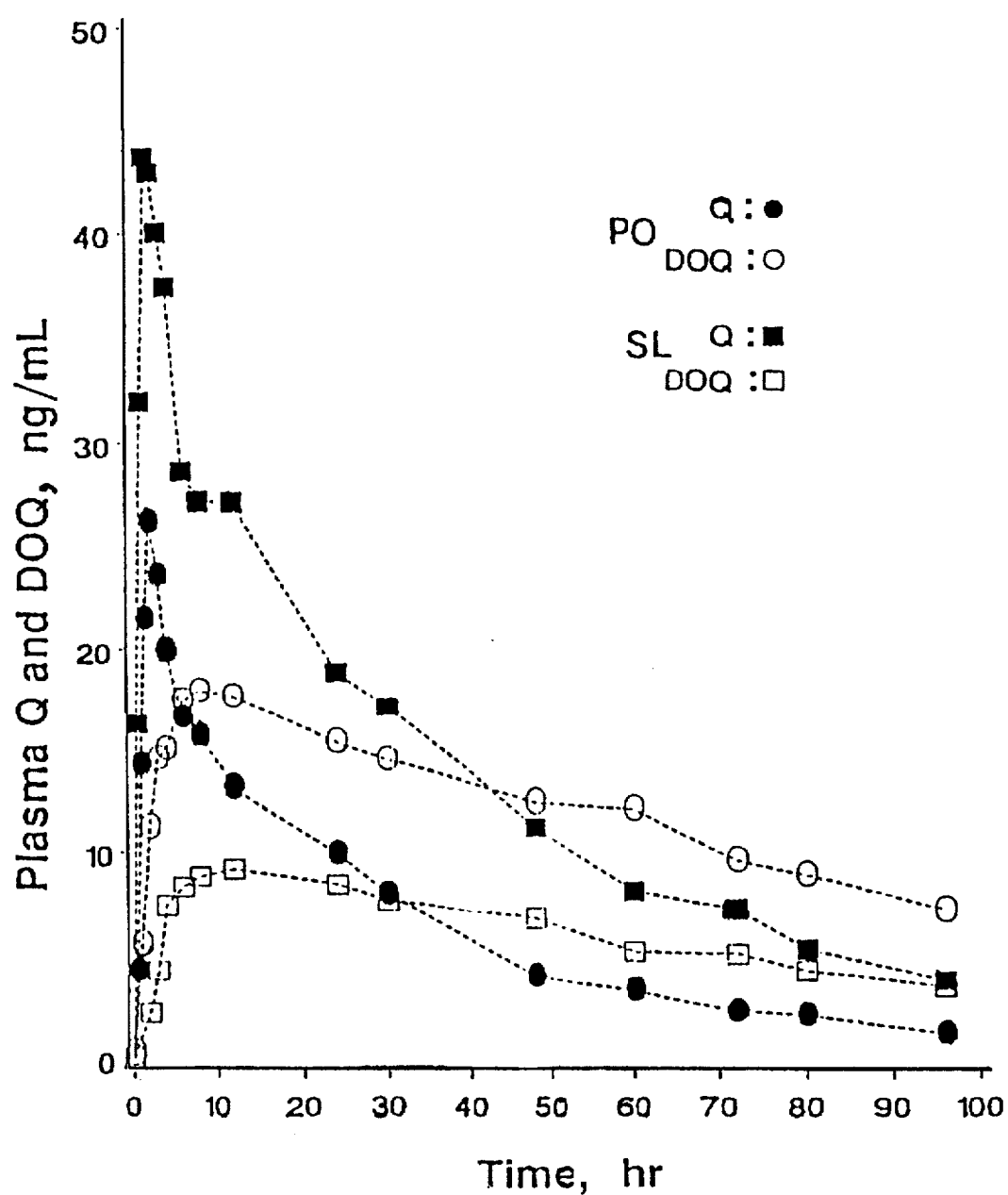
FIG. 1 is a graph illustrating the concentration of quazepam (Q) and N-desalkyl-2-oxoquazepam (DOQ) in the blood plasma over 96 hours following a single sublingual dose (SL) or per oral swallowed dose (PO) of 15 mg of quazepam.
Figure 2:
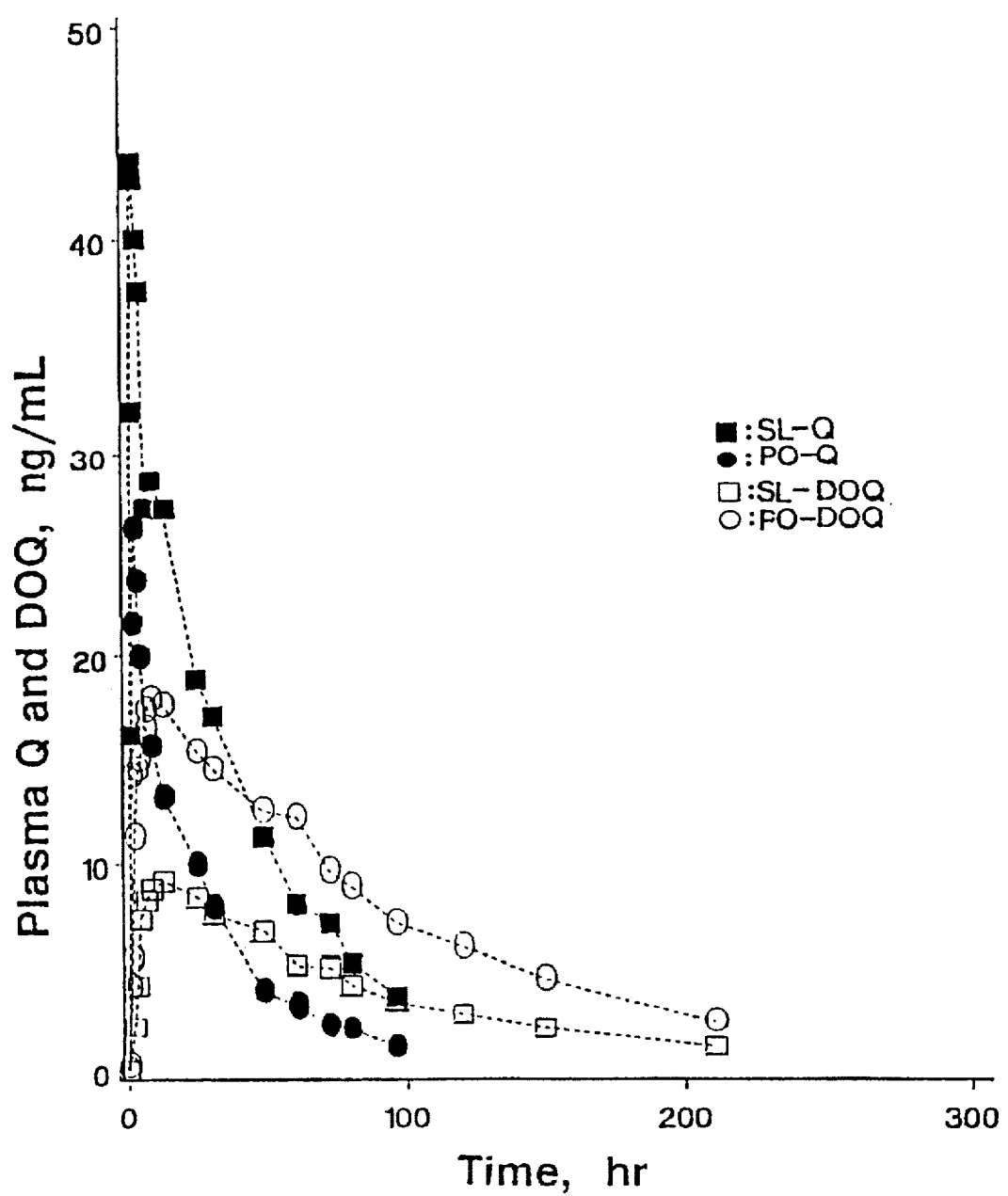
FIG. 2 is a graph illustrating the concentration of quazepam (Q) and N-desalkyl-2-oxoquazepam (DOQ) in the blood plasma over 210 hours following a single sublingual dose (SL) of 15 mg of quazepam or per oral swallowed dose (PO)
Figure 3:
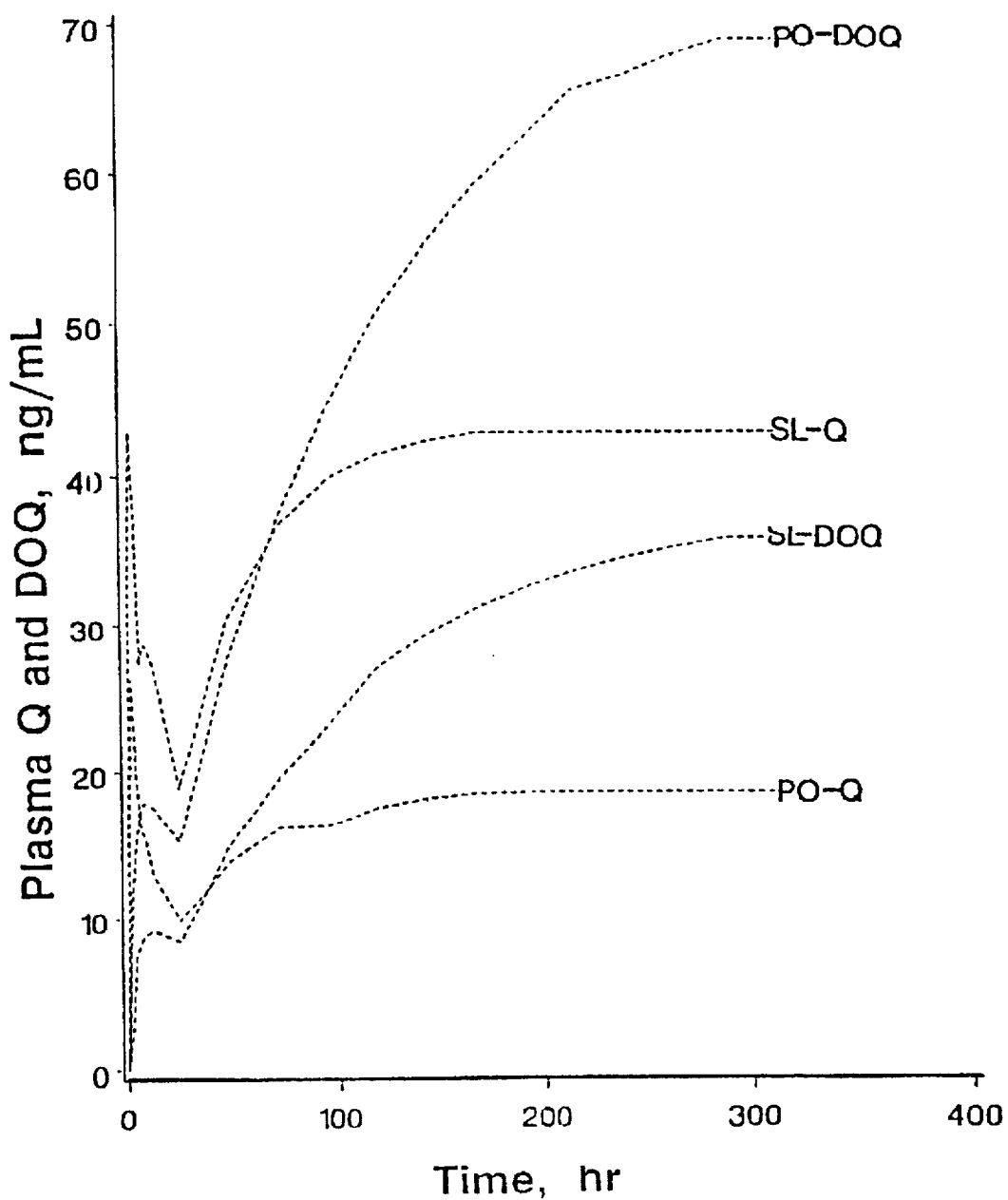
FIG. 3 is a graph of computer simulated concentration levels of quazepam and N-desalkyl-2-oxoquazepam in the blood following sublingual and oral swallowed doses of 15 mg of quazepam once a day for a 15 day period illustrating the marked reduction in accumulated levels of desalkyloxoquazepam with sublingual dosing.

Applicants have unexpectedly and surprisingly discovered that sublingual dosing, in contrast to the usual clinical oral dosing of quazepam, increases the availability of quazepam about 60% while the DOQ drops to about one-half that of the oral quazepam administration levels. In other words, applicants have unexpectedly and surprisingly discovered that the aforementioned undesirable "first pass" augmentation of desalkylation to the DOQ metabolite can be markedly reduced or obviated by sublingual dosing of quazepam. This change in concentrations for the two compounds can be seen with reference to FIG. 1 and FIG. 2 of the drawings where the differences in the parent compound Q and the metabolite DOQ for both the oral and sublingual dosing is shown. In FIG. 3, by use of standard multiple Q dose simulations, the differences in accumulation of Q and DOQ for sublingual versus oral dosing over 15 days is shown. With chronic dosing it is readily apparent that after 15 days the DOQ level, following oral administration, has reached levels that are associated with the threshold for impairing ataxic and incoordination affects (especially if larger doses are given). With sublingual dosing the accumulated levels of DOQ are approximately one-half of the oral dosing and the levels of Q are over twice that of the oral levels.

In Table 1 and Table 2, set forth below, the average pharmacokinetic parameters for both Q and DOQ for both oral and sublingual routes of administration are reported:

TABLE I

AVERAGE PHARMACOKINETIC PARAMETERS OF QUAZEPAM FOLLOWING SUBLINGUAL AND ORAL ADMINISTRATION OF QUAZEPAM (15 mg)

| | Route of Administration of Quazepam | |
|---|---|---|
| Parameter | Sublingual | Oral |
| t1/2 Ka (hr) | 0.27 ± 0.10[a] | 0.77 ± 0.23 |
| t1/2 λ 1 (hr) | 1.44 ± 0.45 | 1.73 ± 0.65 |
| t1/2 λ 2 (hr) | 27.72 ± 7.18 | 24.63 ± 8.35 |
| Lag time (hr)[b] | 0.18 ± 0.05 | 0.52 ± 0.28 |
| Cmax (ng/ml)[b] | 42.35 ± 10.43 | 26.74 ± 6.83 |
| tmax (hr)[b] | 0.78 ± 0.31 | 2.57 ± 1.69 |
| AUC (ng · hr/ml)[b] | 1461.35 ± 298.67 | 472.79 ± 238.92 |
| CL/F (1/hr)[b] | 8.78 ± 5.25 | 37.56 ± 16.89 |

[a]Mean ± SD
[b]Differed significantly from oral dosing (P <0.05)
Legend:
t1/2 = Half-Life
$K_a$ = Absorption
λ 1 = Rapid Distribution
λ 2 = Terminal Elimination
$C_{max}$ = Peak Plasma Concentration
$t_{max}$ = Time to Cmax
AUC = Area Under Plasma Concentration-Time Curve
CL/F = Clearance

TABLE II

AVERAGE PHARMACOKINETIC PARAMETERS OF N—DESALKYL-2-OXOQUAZEPAM FOLLOWING SUBLINGUAL AND ORAL ADMINISTRATION OF QUAZEPAM (15 mg)

| | Route of Administration of Quazepam | |
|---|---|---|
| Parameter | Sublingual | Oral |
| $t_{1/2}$ $K_m$ (hr) | 1.07 ± 0.31[a] | 1.24 ± 0.52 |
| $t_{1/2}$ λ 2 (hr) | 69.30 ± 18.62 | 71.44 ± 21.16 |
| Lag time (hr) | 1.74 ± 0.86 | 0.66 ± 0.32 |
| $C_{max}$ (ng/ml)[b] | 8.18 ± 2.35 | 17.58 ± 4.17 |
| $t_{max}$ (hr) | 7.33 ± 4.15 | 6.17 ± 3.52 |
| AUC (ng · hr/ml)[b] | 949.02 ± 365.74 | 1966.70 ± 410.90 |

[a]Mean + SD
[b]Differed significantly from oral dosing (P <0.05)
Legend:
$t_{1/2}$ = Half-Life
$K_m$ = Formation
λ 2 = Terminal Elimination
$C_{max}$ = Peak Plasma Concentration
$t_{max}$ = Time to $C_{max}$
AUC = Area Under Plasma Concentration-Time Curve The profile in FIGS. 1 and 2 of the drawings clearly shows that there is a first-pass metabolism for Q leading to the attenuated Q levels. On the basis of applicants' pharmacokinetic studies, applicants have discovered that sublingual dosing which bypasses first pass metabolism, minimizes the N-desalkylation metabolic pathway that leads to the formation of the unwanted metabolite, DOQ. This has lead applicants to the sublingual dosing method of the invention which provides for maximization of the important therapeutic effects of the drug. Thus, applicants have discovered the means by which quazepam can be administered such that one can maximize the $BZ_1$ effect and reduce the $BZ_2$ effect of its metabolite (DOQ) and thereby enhance the efficacy in use on humans of this therapeutic drug.

In summary, applicants have discovered the following: (1) The use of sublingual dosing of quazepam to markedly reduce first pass metabolism of the quazepam structure and thereby enhance the $BZ_1$ effect of the drug; and (2) The use of sublingual dosing to increase the $BZ_1-BZ_2$ ratio with acute dosing and repeated dosing over days (since the dosing regimen is reducing the DOQ levels and thus attenuating the many impairing effects of the high affinity slowly metabolized quazepam metabolite). These phenomena resulting from sublingual dosing provide for an unexpected and surprising enhancement of the efficacy and reduction of toxicity of the drug in reducing anxiety and convulsions in humans.

Figure 4:
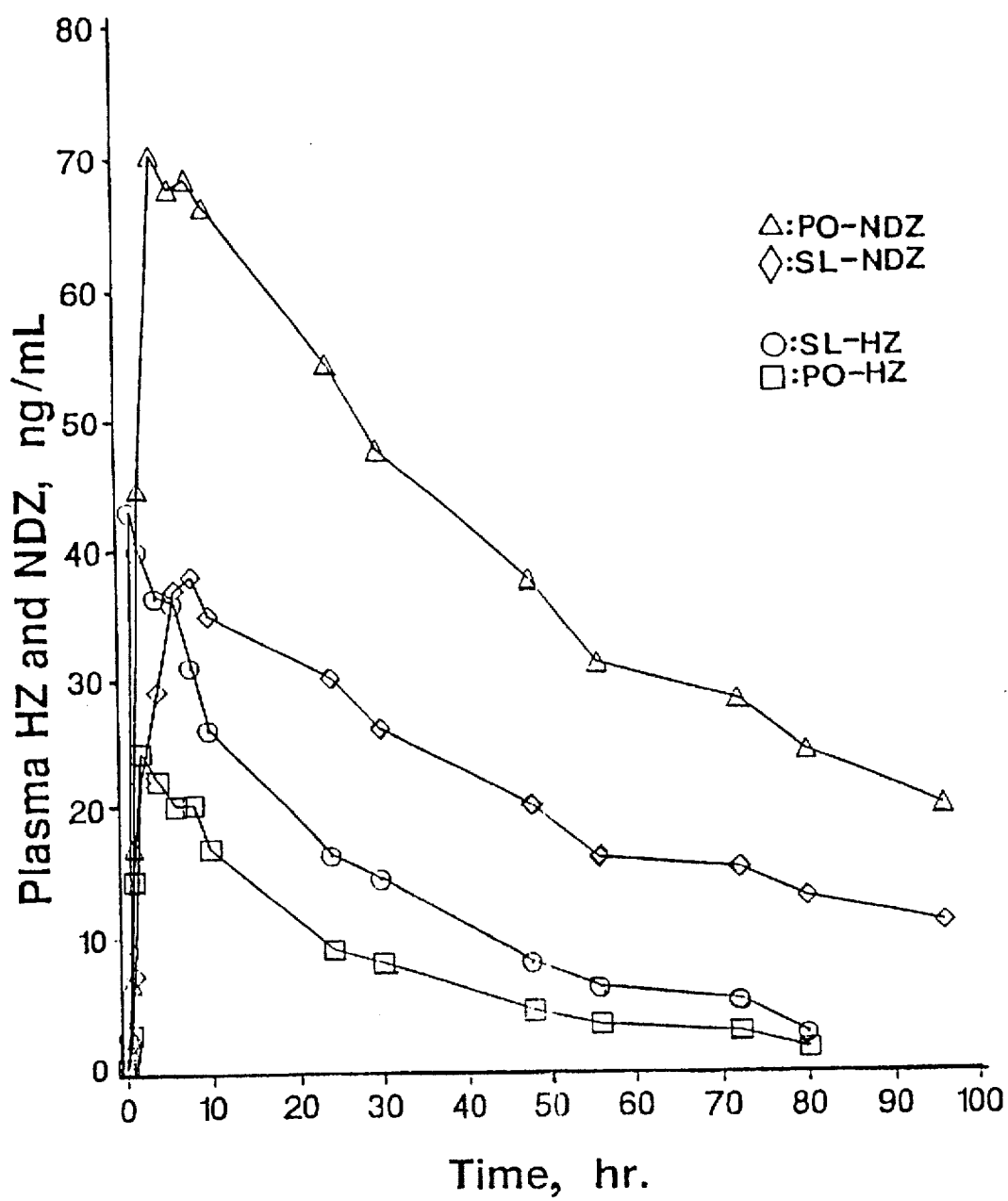
FIG. 4 is a graph illustrating the concentration of halazepam (HZ) and N-desalkyl-3-hydroxy-halazepam (ND) in the blood over 96 hours following a single sublingual dose (SL) or per oral swallowed dose (PO) of 20 mg of halazepam.
Figure 5:
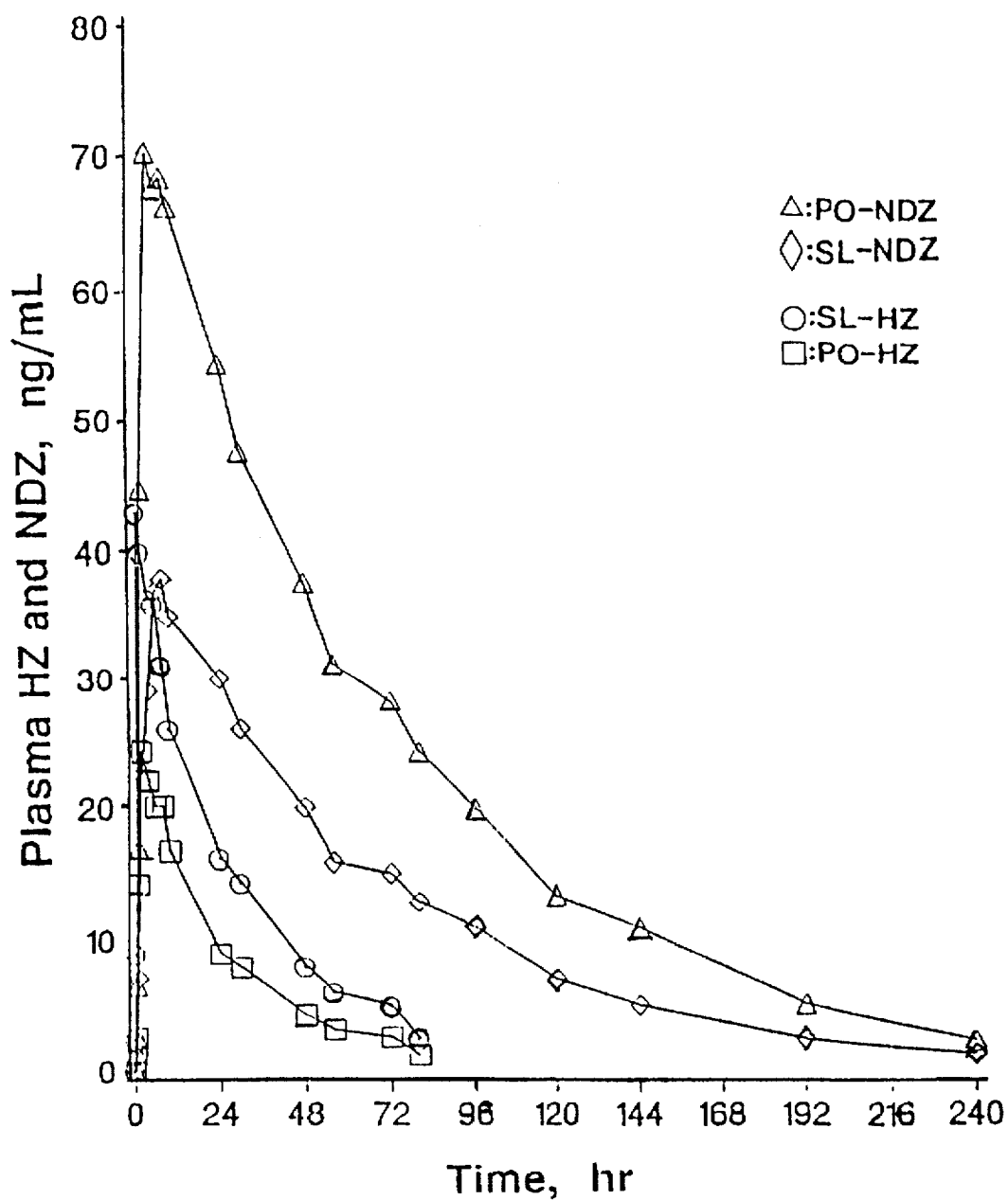
FIG. 5 is a graph illustrating the concentration of halazepam (HZ) and N-desalkyl-3-hydroxy-halazepam (ND) in the blood over 240 hours following a single sublingual dose (SL) or per oral swallowed (PO) of 20 mg of halazepam.
Figure 6:
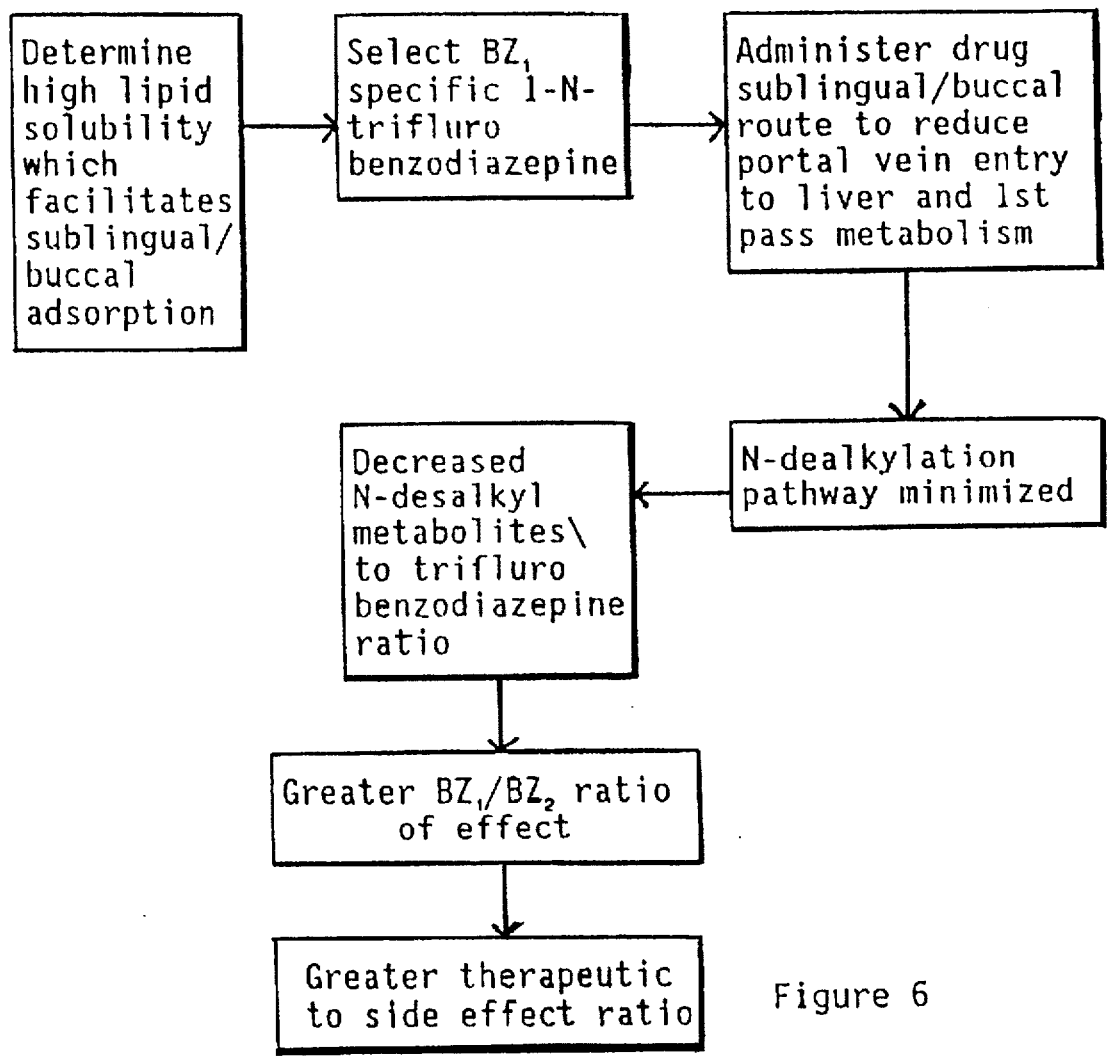
FIG. 6 is a flow chart of the method of the present invention.

With references now to FIGS. 4 and 5, applicants have also tested high $BZ_1$ specific drug halazepam and discovered similar results obtained by sublingual administration thereof: The availability of halazepam was significantly increased thus maximizing the $BZ_1$ effect while reducing the $BZ_1-BZ_2$ metabolite N-desalkyl-hydroxy-halazepam. Applicants thus believe that intraoral administration, either buccal or sublingual, of selected trifluorobenzodiazepines can substantially enhance their therapeutic effect for the reasons set forth herein. Applicants' novel method can be better appreciated with reference to FIG. 6 of the drawings which depicts a flow chart of the steps of the novel therapeutic method.

ALTERNATIVE EMBODIMENT OF THE INVENTION

Thus applicants have made the discovery of the sublingual route of administration for enhancing the $BZ_1$ specific effects of the trifluorobenzodiazepines by inhibiting the formation of unwanted metabolite.

Applicants have shown above that the manner in which the original blood borne trifluorobenzodiazepine drug enters into the liver has a profound effect on the directing of the vector of metabolism for this given species of drugs. This class of benzodiazepines has a desalkylation metabolism. Applicants' findings of the alteration of metabolism by sublingual administration led to the novel discovery that one could alter the steady state metabolic profile of this class of drugs by bypassing the profound early stage desalkylation metabolism that occurred when the swallowed drug entry was via the portal vein metabolic pathway. This discovery required projection of acute dosing pharmacokinetics to fully understand and project steady state pharmacokinetics that document the robust advantages of the sublingual administration route in: (1) shifting to a reduced desalkylation metabolic profile; (2) reducing the production of unwanted non-specific metabolites; and (3) thereby, enhancing an advantageous ratio $BZ_1$ specific to the nonspecific $BZ_1$, $BZ_2$ metabolites.

To the original discovery described hereinabove that N-desalkylation of trifluorobenzodiazepines could be markedly reduced by sublingual administration, applicants now have discovered that desalkylation of other drugs can be reduced by sublingual or buccal administration. These other drugs also have unwanted or toxic desalkylation metabolites.

For example, propoxyphene ((+)-α-4-(dimethylamino)-3-methyl-1,2-diphenyl-2-butanol propionate hydrochloride), a widely used, prescribed, oral analgesic is frequently associated with poisonings and death. A major concern is that accumulating levels of the non-analgesic metabolite norpropoxyphene has cardiac conduction depressing effects that are a source of cardiotoxicity. The wanted analgesic effects of propoxyphene are limited by its short half life, whereas, the unwanted norpropoxyphene metabolite has a half life of 2-3 times that of the propoxyphene. With multiple dosing the norpropoxyphene metabolite half life may increase to 39 hours, thus accumulating over days of use.

Propoxyphene is N-desalkylated similarly to the trifluorobenzodiazepines. Since its desalkylated metabolite norpropoxyphene has the potential to induce cardiac conduction delay with toxic consequences at accumulated doses, applicants explored the sublingual route of administration. Two normal subjects were given 65 mg of propoxyphene both by per oral swallowed and sublingual administration.

Figure 7:
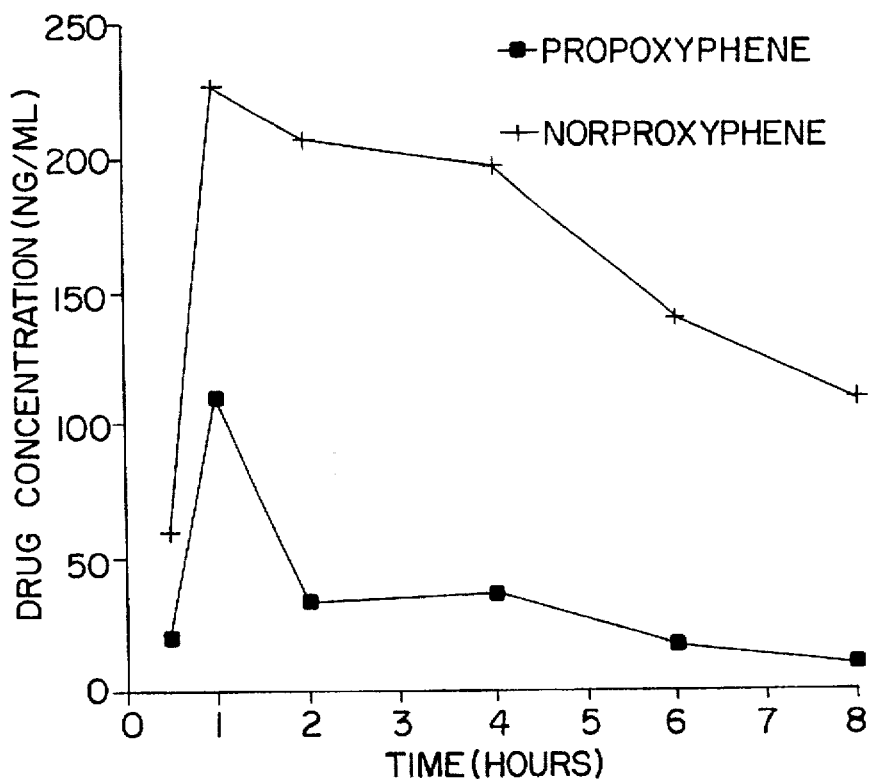
FIG. 7 is a graph illustrating the concentration of propoxyphene and norpropoxyphene in the blood plasma over 8 hours following a single per oral swallowed dose of 65 mg of propoxyphene.
Figure 8:
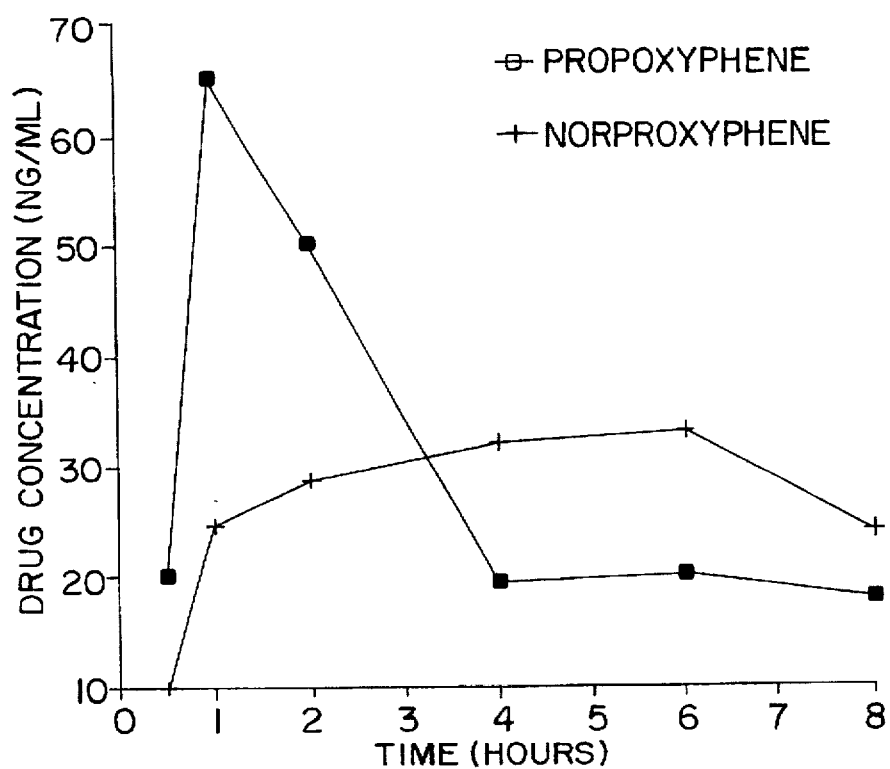
FIG. 8 is a graph illustrating the concentration of propoxyphene and norpropoxyphene in the blood plasma over 8 hours following a single sublingual dose of 65 mg of propoxyphene in the same subject as seen in FIG. 7.
Figure 9:
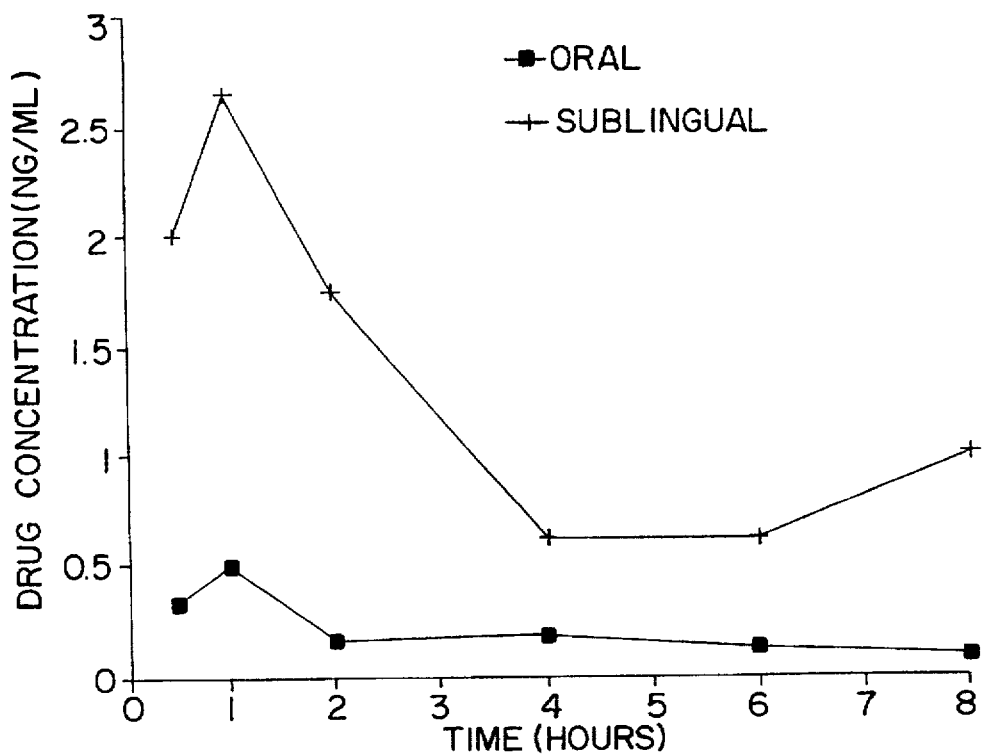
FIG. 9 is a graph illustrating the ratio of propoxyphene concentration to norpropoxyphene concentration for both per oral swallowed and sublingual administration in the subject seen in FIGS. 7 and 8.
Figure 10:
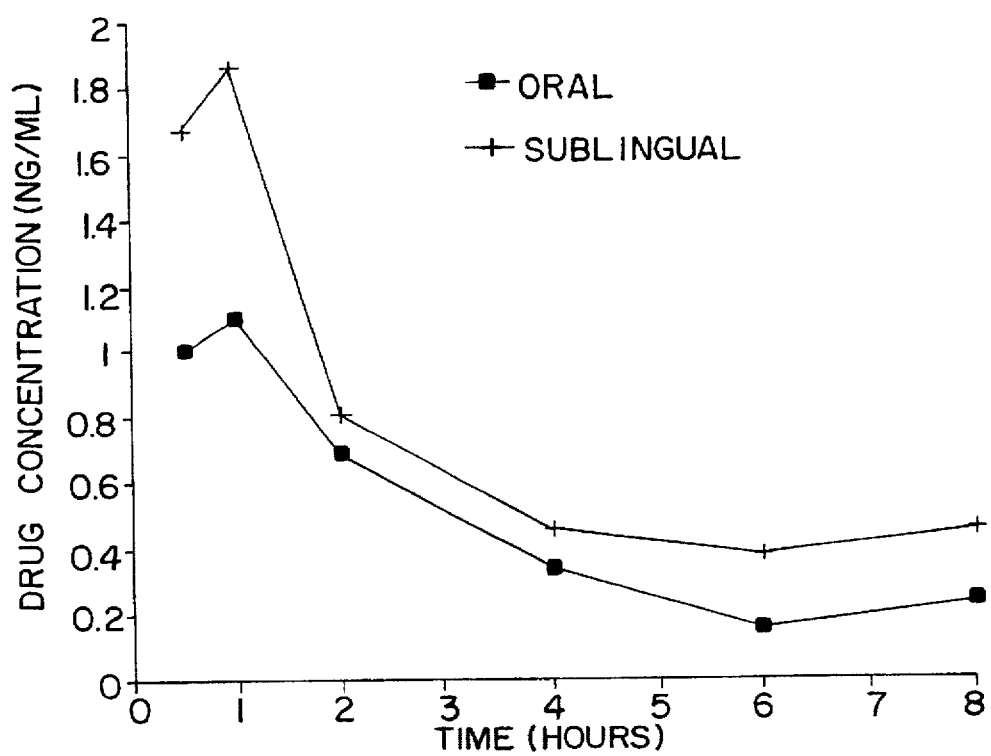
FIG. 10 is a graph illustrating the ratio of propoxyphene concentration to norpropoxyphene concentration for both per oral swallowed and sublingual administration in another subject in addition to that shown in FIGS. 7 and 8.

FIGS. 7 and 8 demonstrate the propoxyphene and norpropoxyphene plasma concentrations for (1) per oral swallowed and (2) sublingual administration in a single subject over an eight (8) hour period. FIG. 9 illustrates the propoxyphene/norpropoxyphene ratios for sublingual and oral dosing over time for the subject of FIGS. 7 and 8. FIG. 10 illustrates the same ratios for a second subject under the same test conditions. The increase in wanted parent compound to unwanted metabolite for sublingual dosing is readily apparent. Thus, sublingual dosing reduces propoxyphene desalkylation metabolism thereby increasing the therapeutic toxic ratio.

As a further example, another drug that has N-desalkylation to an unwanted metabolite is chlorimipramine (CL) which is metabolized to desmethylchlorimipramine (DMCL).

Chlorimipramine is a specific inhibitor of serotonin uptake which is a desired property in the treatment of obsessive compulsive disorders, whereas desmethylchlorimipramine is a potent inhibitor of norepinephrine. Thus, the DMCL metabolite in many individuals accumulates to levels much greater than CL, and thus qualitatively changes the biochemical effect during treatment. In addition, the accumulation of DMCL poses additional potential toxicity from its cardiac conduction slowing properties similar to that of norproxyphene.

Applicants administered 25 mg of CL to normal subjects per orally and sublingually. In subjects who had a high desalkylation level, sublingual administration markedly reduced the unwanted metabolite DMCL thereby increasing the wanted parent compound CL to unwanted metabolite DMCL ratio. Other subjects did not demonstrate this effect. Therefore, the sublingual administration would be important only for certain individual patients who were shown to have unfavorable ratios.

SECOND ALTERNATIVE EMBODIMENT OF THE INVENTION

In a study of mCPP plasma levels that were achieved by oral dosing of human subjects with nefazodone, the area under the curve from 1 hour to 6 hours for two subjects revealed a nefazodone/mCPP ratio of 1.93, slightly higher than the ratio described by Walsh et al., supra. In contrast, sublingual administration of nefazodone (which included an incidental amount of buccal administration) to human subjects resulted in a nefazodone/mCPP ratio from 1 hour to 6 hours of 3.82. Thus, approximately a 100% increase in the ratio of wanted to unwanted metabolites was achieved with sublingual administration of nefazodone, as compared to oral administration of nefazodone, and the same magnitude of increase should also be achieved with buccal administration of nefazodone. Because nefazodone and mCPP have a short half-life, values after 6 hours have little contribution to the plasma levels. The plasma levels before 1 hour were variably below the detection level and/or highly variable so they were not included in the values reported.

More importantly, the peak mCPP plasma levels (hereinafter, abbreviated as Cmax) were considerably more elevated from the oral dosing versus the sublingual dosing. One subject had a peak level of 51 ng/ml for sublingual dosing compared to 145 ng/ml for oral dosing. The other subject had a 21 ng/ml Cmax mCPP level for sublingual dosing versus a 48 ng/ml mCPP for oral dosing. Thus, the Cmax levels for mCPP were approximately 3 times greater for the oral dosing than for the sublingual dosing. These values are significant in that Zohar et al., supra, reported that levels of 26-35 ng/ml induced obsessional and anxiolytic effects, in obsessional patients.

To compare sublingual to oral administration, the mean average values for the two subjects for mCPP for sublingual administration (SL) and for oral administration (PO) at 1-6 hours, are reported below in Table III.

TABLE III

PHARMACOKINETICS OF NEFAZODONE (NEF) AND mCPP AFTER 50 mg SUBLINGUAL AND ORAL DOSES OF NEFAZODONE

| | Subject 1 | | | | Means for Both Subjects | | | |
|---|---|---|---|---|---|---|---|---|
| | NEF | | mCPP | | NEF | | mCPP | |
| Parameteres | SL | PO | SL | PO | SL | PO | SL | PO |
| $C_{max}$ (ng/ml) | 200 | 291 | 21 | 48 | 174 | 226 | 33 | 97 |
| $AUC_{6 hr}$ (ng · hr/ml) | 568 | 420.3 | 44 | 84.3 | 435.5 | 521 | 114 | 270 |

The abbreviations used in Table III are the same as those used in Tables I and II above.

Figure 11:
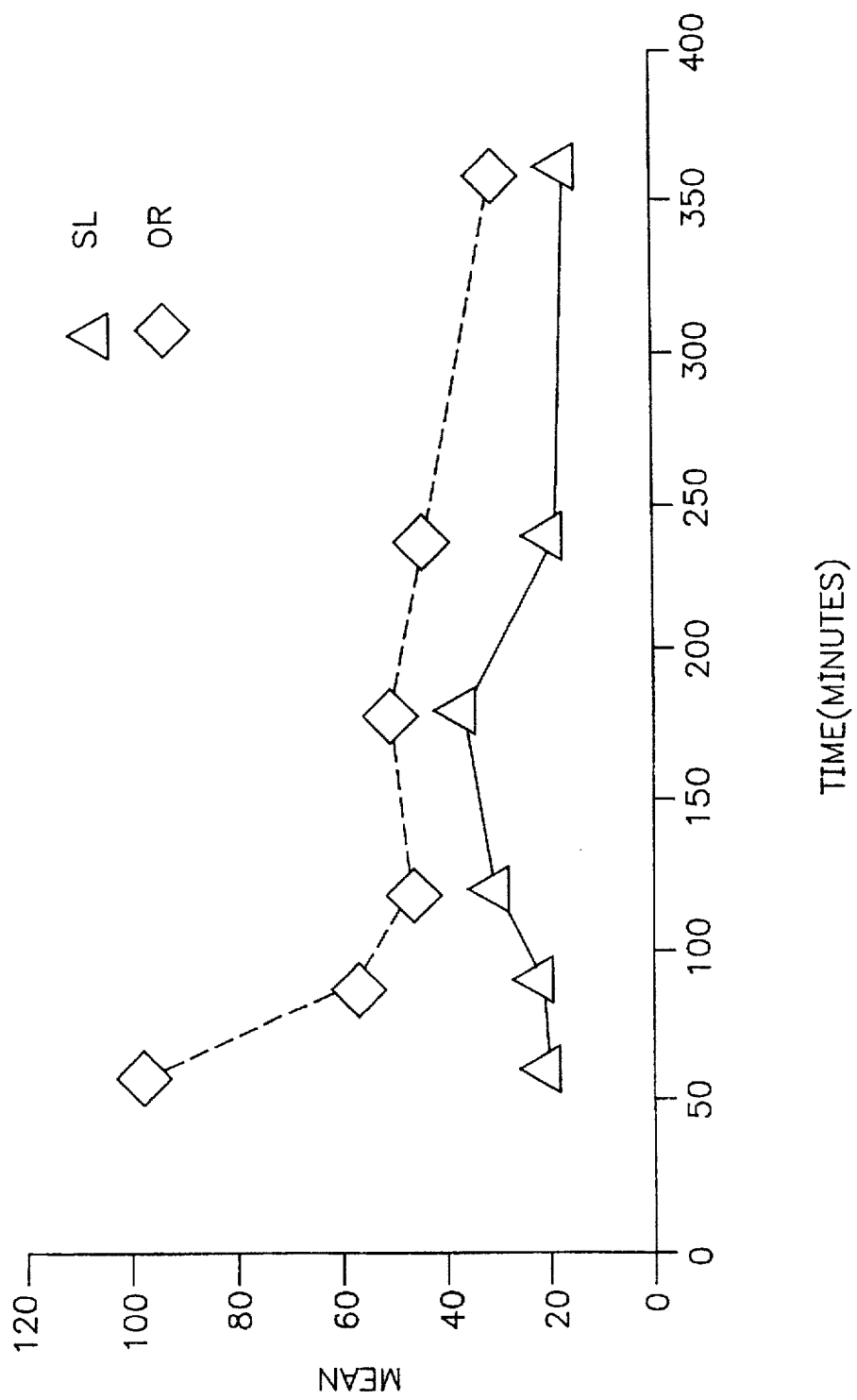
FIG. 11 is a graph illustrating the sublingual (SL) versus the oral (OR) dosing for m-chlorophenylpiperazine (hereinafter, abbreviated as MCPP) plasma.
Figure 12:
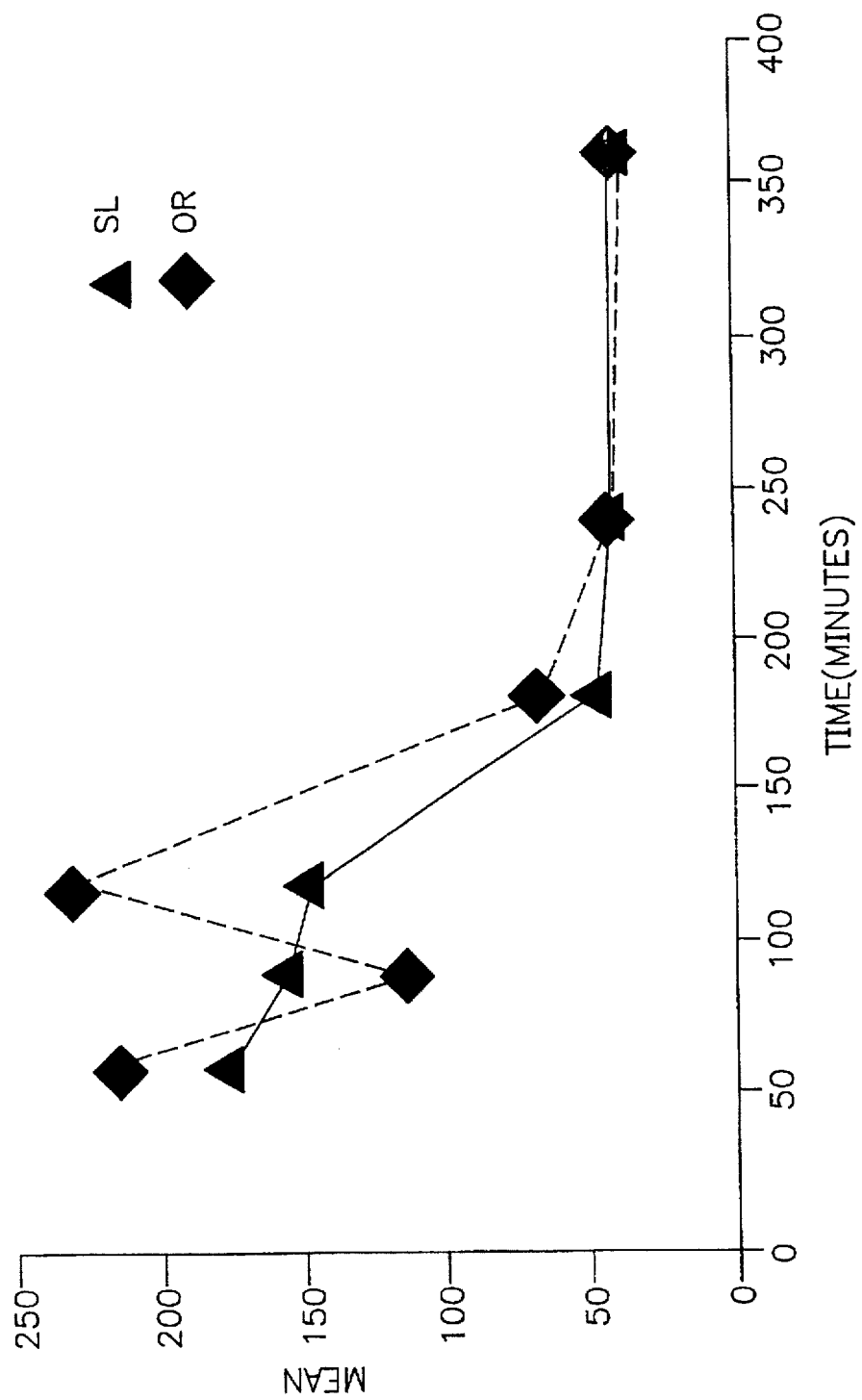
FIG. 12 is a graph illustrating the sublingual (SL) versus the oral (OR) dosing for nefazodone plasma.

At 1 hour, there was a 5 times greater ratio from oral as compared to sublingual administration for mCPP, which decreased to a 3 times greater ratio at 1-½ hours, and gradually reduced after that (also, see FIG. 11). In contrast, the nefazodone levels were comparable in the ratios for oral as compared to sublingual administration (also, see FIG. 12). Thus, the sublingual/oral ratio of nefazodone appeared slightly above 1.

Conditions such as obsessive compulsive syndrome and panic disorder, which have a large overlap with anxiety disorders, are susceptible to precipitation and worsening with mCPP. The present discovery indicates that mCPP, an unwanted metabolite of nefazodone, and especially the early peak mCPP levels, can be reduced by sublingual administration of nefazodone, and also should be reduced by buccal administration of nefazodone.

It has been demonstrated that mCPP, an unwanted metabolite, induces a rapid onset of adverse consequences, and at times long-lasting adverse consequences, including obsessional ruminations and anxiety as reported by Zohar et al. With the present invention, it has been demonstrated that the rapid onset of mCPP maximal peak levels can be remarkably reduced by sublingual administration of nefazodone, and should also be reduced by buccal administration of nefazodone. This demonstration of changes with the mCPP metabolite of nefazodone is to be compared with the above data for trifluorobenzodiazepan and chloroimipramine, in which the accumulation of unwanted metabolites may require hours or days to manifest its effect, and with the rapid rise in plasma level of certain unwanted metabolites from oral administration mCPP that is associated with an intense, rapid induction of unwanted effects, the mCPP peak effects occurring within three hours, as reported by Zohar et al. Once precipitated, the adverse effects can last for hours.

In summary, the discovery that the sublingual method of administration for trifluorobenzodiazpenes and propoxyphene reduced the adverse effects of unwanted metabolites was based on the reduction of the gradual accumulation of the unwanted metabolites to adverse cumulative concentration levels. On the other hand, in the case of mCPP, the unwanted metabolites levels measured after the oral administration nefazodone far exceeded the 25-35 ng/ml of mCPP that manifests onset of adverse precipitous symptoms in susceptible panic disorder patients as reported by Zohar et al. More importantly, the ratio of peak oral to peak sublingual mCPP blood levels was found to be approximately 3 times that reported by Zohar et al. In contrast, the ratio of the parent compound, nefazodone, levels for the oral to sublingual ratio was found to be near 1-1.3 times that reported by Walsh et al.

Also, trazodone, an antidepressant with a very close molecular structure to nefazodone, is similarly metabolized to the mCPP unwanted metabolite and is a candidate for sublingual or buccal administration to reduce the unwanted metabolite to parent drug ratio. In other words, sublingual or buccal administration of trazodone should increase the ratio of parent medicament to unwanted metabolite made available to the human body, including the central nervous system.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for administering medicament to the human body, including the central nervous system, wherein a therapeutically effective amount of said medicament is intraorally administered to a human, the improvement comprising the steps of:

a. selecting a medicament that is metabolized into an unwanted or adversive metabolite that is increased by gastrointestinal tract absorption and subsequent portal vein entry to the liver;

b. placing the medicament in a suitable intraoral formulation;

c. intraorally administering a therapeutically effective amount of the intraoral formulation so as (i) to bypass the gastrointestinal tract absorption and subsequent portal vein entry to the liver and (ii) thereby to decrease formation of the unwanted metabolite;

d. increasing the ratio of medicament to the unwanted metabolite made available to the human body, including the central nervous system; and e. utilizing this intraoral method over a period of one or more doses to achieve sustained high levels of the medicament relative to the unwanted metabolite.

2. The method of claim 1, wherein the medicament comprises bupropion.

3. The method of claim 1, wherein the medicament comprises trazodone.

4. The method of claim 1, wherein the intraoral method comprises sublingual or buccal administration.

* * * * *